United States Patent
Cua et al.

(10) Patent No.: US 7,820,168 B2
(45) Date of Patent: Oct. 26, 2010

(54) TREATMENT OF DIABETES USING ANTIBODIES TO IL-23, IL-23 RECEPTOR AND IL-17

(75) Inventors: Daniel J. Cua, Boulder Creek, CA (US); Robert A. Kastelein, Redwood City, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/305,748

(22) Filed: Dec. 16, 2005

(65) Prior Publication Data

US 2006/0134112 A1 Jun. 22, 2006

Related U.S. Application Data

(60) Provisional application No. 60/637,917, filed on Dec. 20, 2004.

(51) Int. Cl.
*A61K 39/395* (2006.01)
(52) U.S. Cl. ...................... 424/145.1; 514/866
(58) Field of Classification Search ............... None
See application file for complete search history.

(56) References Cited

U.S. PATENT DOCUMENTS

| | | | | |
|---|---|---|---|---|
| 5,827,513 | A * | 10/1998 | Bond et al. | 424/85.2 |
| 6,706,264 | B1 | 3/2004 | Leonard et al. | |
| 2003/0017617 | A1 | 1/2003 | Chirica et al. | |
| 2003/0206874 | A1* | 11/2003 | Doyle et al. | 424/49 |
| 2004/0213761 | A1 | 10/2004 | Bowman et al. | |
| 2004/0258686 | A1 | 12/2004 | Chirica et al. | |

FOREIGN PATENT DOCUMENTS

| | | | |
|---|---|---|---|
| WO | WO 01/18051 A | | 3/2001 |
| WO | WO 2004042009 A2 * | | 5/2004 |
| WO | WO 2004/071517 A | | 8/2004 |
| WO | WO 2004/081190 A | | 9/2004 |
| WO | WO 2004/101750 A | | 11/2004 |
| WO | WO 2005010044 A2 * | | 2/2005 |

OTHER PUBLICATIONS

Gerich et al., MedGenMed. Aug. 26, 2004;6(3 Suppl).*
Atkinson et al, Nature, 1999, V.5, pp. 601-604.*
Whitty et al., Chem. Biol. Apr. 1999;6(4):R107-18.*
Casset et al., Biochemical and Biophysical Research Communications, 307:198-205, 2003.*
Monnet et al., J. Biol. Chem. 274 (1999) 3789-3796.*
Rothe et al., Diabetologia. Jun. 1997;40(6):641-6.*
Bergholdt et al., J Med Genet. Apr. 2004;41(4):e39.*
Larger et al., Diabetes Care. Jul. 2004;27(7):1842-3.*
The Merck Manual of Diagnosis and Therapy, (Mark Beers and Robert Berkow, eds., Published by Merck Research Laboratories, 17th ed., 1999, pp. 165-171.*
"The Diabetes Prevention Trial Type I Diabetes Study Group", N Engl J Med. May 30, 2002;346(22):1685-91.*
Kobayashi et al., Diabetes. May 1996;45(5):622-6.*
Goldsby et al., Immunology, 5th Ed., W.H. Freeman and Co., pp. 462-463 (2002).*
Webster's New World Dictionary, Third College Edition, 1988, see p. 1067.*
Jovanovic et al., J Immunol. Apr. 1, 1998;160(7):3513-21.*
Zozulinska et al., Diabetologia. Jan. 1999;42(1):117-8.*
Chen et al., Diabetologia. Mar. 2001;44(3):325-32.*
Rabinovitch et al., Diabetes Metab Rev. Jun. 1998;14(2):129-51.*
Tennenberg et al., Arch Surg. Nov. 1999;134(11):1229-33.*
Vukkadapu et al., Physiol Genomics. Apr. 14, 2005;21(2):201-11.*
Martin-Orozco et al., Eur J Immunol. Jan. 2009;39(1):216-24.*
Jain et al., J Exp Med. Jan. 21, 2008;205(1):207-18.*
Emamaullee et al., Diabetes. Jun. 2009;58(6):1302-11.*
Cua, et al. (2003) *Nature* 421(6924):744-748 "Interleukin-23 rather than interleukin-12 is the critical cytokine for autoimmune inflammation of the brain".
Elkins, et al. (2002) *Infection Immunity* 70(4):1936-1948 "In Vivo Clearance of an Intracellular Bacterium, *Francisella tularensis* LVS, Is Dependent on the p40 Subunit of Interleukin-12 (IL-12) but Not on IL-12 p70".
Frucht (2002) *Sci STKE* 114:pe1 (pp. 1-3) "IL-23: a cytokine that acts on memory T cells".
Hutchings et al., (1990) *J. Autoimmun*. Issue 3, Suppl. 1, pp. 101-109 "The involvement of Ly2+ T cells in beta cell destruction".
Lund et al., (1990) *Nature* 345(6277):727-729 "Prevention of insulin-dependent diabetes mellitus in non-obese diabetic mice by transgenes encoding modified I-Aβ-chain or normal I-Eα-chain".
Murphy, et al. (2003) *J. Exp. Med*. 198(12):1951-1957 "Divergent Pro- and Antiinflammatory Roles for II-23 and IL-12 in Jiont Autoimmune Inflammation".
Oppmann, et al. (2000) *Immunity* 13(5):715-725 "Novel p19 Protein Engages IL-12p40 to Form a Cytokine, IL-23, with Biological Activites Similar as Well as Distinct from IL-12".
Parham, et al. (2002) *J. Immunol*. 168:5699-5708 "A receptor for the heterodimeric cytokine IL-23 is composed of IL-12Rβ1 and a novel cytokine receptor subunit, IL-23R".
Slattery et al., (1990) *Nature* 345:724-726 "Prevention of diabetes in non-obese diabetic I-Ak transgenic mice".
Trinchieri, et al. (2003) *Immunity* 19(5):641-644 "The IL-12 family of heterodimeric cytokines: new players in the regulation of T cell responses".
Wiekowski, et al. (2001) *J. Immunol*. 166(12):7563-7570 "Ubiquitous transgenic expression of the IL-23 subunit p19 induces multiorgan inflammation, runting, infertility, and premature death".
Aggarwal et al. (2003) *J. Biol. Chem*. 278:1910-1914 "Interleukin-23 promotes a distinct CD4 T cell activation state characterized by the production of Interleukin-17".
Feili-Hariri et al. (2002) *Eur. J. Immunol*. 32:2021-2030 "Regulatory Th2 response induced following adoptive transfer of dendritic cells in prediabetic NOD mice".

* cited by examiner

*Primary Examiner*—Zachary Skelding
(74) *Attorney, Agent, or Firm*—Gregory R. Bellomy

(57) ABSTRACT

The instant specification provides methods of treatment for inflammatory and autoimmune disorders of the metabolic system. The instant specification also provides methods of diagnosis.

20 Claims, No Drawings

TREATMENT OF DIABETES USING ANTIBODIES TO IL-23, IL-23 RECEPTOR AND IL-17

This filing is a U.S. Patent Application which claims benefit of U.S. Provisional Patent Application No. 60/637,917, filed Dec. 20, 2004, which is incorporated herein by reference.

FIELD OF THE INVENTION

The present invention relates generally to uses of mammalian cytokine molecules and related reagents. More specifically, the invention relates to a cytokine that mediates disorders of the metabolic system, in particular diabetes.

BACKGROUND OF THE INVENTION

Diabetes mellitus is a disease of the metabolic dysregulation, most notably dysregulation of glucose metabolism, accompanied by long-term vascular and neurologic complications. This metabolic disorder consists of five classes of diabetes: Type 1 diabetes mellitus, also known as insulin-dependent diabetes mellitus or IDDM; Type 2 diabetes mellitus, also know as non-insulin-dependent diabetes mellitus or NIDDM; secondary diabetes, due to other conditions including pancreatitis, endocrine diseases, or ingestion of certain medications; impaired glucose tolerance; and gestational diabetes mellitus (see, e.g., Report of the Expert Committee on the diagnosis and classification of Diabetes mellitus, (1997) *Diabetes Care* 20:1183).

NIDDM has a prevalence of approximately 6.6% of the US population. The clinical characteristics include onset after 40 years of age, correlation with obesity, and insulin resistance often present with inadequate insulin production. IDDM is occurs with much less frequency than NIDDM. The clinical characteristics of IDDM include juvenile onset, prone to ketosis, absolute insulin deficiency where exogenous insulin is necessary for survival, and the presence of anti-islet cell antibodies.

IDDM is known to have a prolonged asymptomatic of preclinical period (see, e.g., Ziegler, et al. (1990) *Diabetes Care* 13:762). During this preclinical period, insulin-producing beta cells of the pancreas are progressively destroyed. A normal pancreas contains 1.0-1.5 million islet cells, with 80% of these responsible for insulin secretion. In a clinically presenting IDDM patient, typically 90% of the beta islet cells have been destroyed. Islet Cell Antibodies (ICAs) have been detected as long as 10 years before the clinical appearance of IDDM (see, Ziegler, supra.).

T lymphocyte mediated immune responses are important in the development of most autoimmune diseases, including IDDM, and in transplant and tumor rejection in mammals (see, e.g., Slattery et al., (1990) *Nature* 345:724-726; Lund et al., (1990) *Nature* 345:727-729; and Hutchings et al., (1990) *J. Autoimmun.* 1:101 -109). The destruction of the beta islet cells is believed to be due to an autoimmune response due to T lymphocyte infiltration of the pancreas.

The non-obese diabetic (NOD) mouse is also known to develop IDDM. Spontaneous IDDM occurs with an incidence of 70-90% in female NOD mice at about 18-25 weeks of age. Because this disease exhibits all of the pathological and autoimmune manifestations of the human disease, NOD mice serve as an excellent model for the identification of agents that might prevent IDDM or ameliorate the effects of the disease. IL-10 and antagonists of IL-12 have been shown to lessen the autoimmune component of IDDM in NOD mice (see, U.S. Pat. Nos. 5,827,513 and 6,706,264).

Interleukin-23 (IL-23) is a heterodimeric cytokine comprised of two subunits, i.e., p19 and p40. The p19 subunit is structurally related to IL-6, granulocyte-colony stimulating factor (G-CSF), and the p35 subunit of IL-12. The p40 subunit is also part of the cytokine IL-12, which is composed of p35 and p40. IL-23 mediates signaling by binding to a heterodimeric receptor, comprised of IL-23R and IL-12beta1. The IL-12beta1 subunit is shared by the IL-12 receptor, which is composed of IL-12beta1 and IL-12beta2. A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of IL-12, but also of IL-23 (Oppmann, et al. (2000) *Immunity* 13:715-725; Wiekowski, et al. (2001) *J. Immunol.* 166:7563-7570; Parham, et al. (2002) *J. Immunol* 168:5699-708; Frucht (2002) Sci STKE 2002, E1-E3; Elkins, et al. (2002) *Infection Immunity* 70:1936-1948). IL-23 is known to be necessary for maintaining the chronic inflammation response.

Recently, it has been shown that IL-23 plays a critical role at the end stage of autoimmune mediated disorders such as multiple sclerosis and rheumatoid arthritis (see, Cua, et al. (2003) *Nature* 421:744-748; and Murphy, et al. (2003) *J. Exp. Med.* 198:1951-1957.). IL-23 preferentially induces the proliferation of memory T cells, as well as the production of inflammatory mediators, IL-17 and TNFα, from these memory T cells, critical cytokines in inflammatory and autoimmune disorders (see, e.g., Cua, supra; Murphy, supra; and Trinchieri, et al. (2003) *Immunity* 19:641-644.).

Most current methods to treat the autoimmune inflammatory aspect of IDDM involve the use of broad immunosuppressive agents such as azathioprine, prednisone, and cyclosporin. Such agents, however, can cause damage to liver, kidney, and other organs, and have the undesirable effect of impairing immune protection against infection and other diseases.

There is an unmet need to treat and/or prevent inflammatory and autoimmune disorders, e.g., diabetes in a less toxic manner. The present invention fulfills this need by providing methods of using antagonists of IL-23 or IL-23R.

SUMMARY OF THE INVENTION

The present invention is based on the observation that antagonist of IL-23 modulates autoimmune inflammatory conditions and disorders associated with the metabolic system, in particular diabetes mellitus.

The present invention provides a method of treating an individual predisposed to an IL-23 mediated autoimmune disorder of the metabolic system comprising administering an effective amount of an antagonist of IL-23 or IL-23R. In another aspect, the present invention provides the above method wherein the disorder is a metabolic disorder. In a further embodiment, the disorder comprises diabetes mellitus. Also provided is an antagonist that specifically binds to a polypeptide or nucleic acid of IL-23p19 or IL-23R. In addition, the invention provides the above method wherein the agonist or antagonist comprises a nucleic acid or small molecule; as well as the above method wherein the nucleic acid comprises anti-sense nucleic acid or small interfering RNA (siRNA).

In another embodiment, the present invention provides a method of treating an IL-23 mediated disorder comprising administering an effective amount of an antagonist of IL-23 or IL-23R, wherein the antagonist is an antigen binding fragment of an antibody or a soluble receptor derived from IL-23R; or the above method wherein the antagonist is a polyclonal antibody; a monoclonal antibody; a humanized antibody or binding fragment thereof, an Fab, Fv, or F(ab')$_2$ fragment; a single chain antibody; a peptide mimetic of an antibody; or is detectably labeled.

Yet another aspect of the present invention provides the above method, wherein the antagonist if IL-23 or IL-23R is co-administered with an: IL-12 antagonist; TNFα antagonist; IL-6 antagonist; IL-17 antagonist; or IL-10 agonist.

The antagonist of IL-23 or IL-23R can also be administered with a broad immunosuppressive therapeutic agent. In a further embodiment, the immunosuppressive therapeutic agent is azathioprine, prednisone, or cyclosporin.

The present invention encompasses a method of treating an individual exhibiting signs of impaired glucose homeostasis to prevent development of diabetes mellitus, the method comprising administering to the individual an effective amount of an antagonist of IL-23 or IL-23R. Impaired glucose homeostasis is measured by plasma glucose levels either during fasting or after a glucose load. In another embodiment, the plasma glucose levels are between 110 to 126 mg per dL during fasting; between 140 and 200 mg per dL after a glucose load.

In yet a further embodiment The antagonist of IL-23 or IL-23R is an antibody or an antigen binding fragment thereof including: a polyclonal antibody; a monoclonal antibody; a humanized antibody; an Fab, Fv, or F(ab')$_2$ fragment; a single chain antibody a peptide mimetic of an antibody; or is detectably labeled. The antibody or antigen binding fragment thereof is co-administered with an immunosuppressive agent including: prednisone; azathioprine; or cyclosporin.

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. Definitions.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of IL-23 or IL-23R antagonist to a human or animal subject, a cell, tissue, physiological compartment, or physiological fluid. "Treatment of a cell" also encompasses situations where the IL-23 or IL-23R antagonist contacts IL-23R complex (IL-23R/IL-12Rbeta1 heterodimer), e.g., in the fluid phase or colloidal phase, but also situations where the agonist or antagonist does not contact the cell or the receptor.

"Binding composition" refers to a molecule, small molecule, macromolecule, antibody, a fragment or analogue thereof, or soluble receptor, capable of binding to a target. "Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive, capable of binding to a target. "Binding" may be defined as an association of the binding composition with a target where the association results in reduction in the normal Brownian motion of the binding composition, in cases where the binding composition can be dissolved or suspended in solution.

A "classical TH1-type T cell" is a T cell that expresses interferon-gamma (IFNγ) to an extent greater than expression of each of IL-4, IL-5, or IL-13, while a "classical TH2-type T cell" is a T cell that expresses IL-4, IL-5, or IL-13, each to an extent greater than expression of IFNγ. "Extent" is typically 4-fold or more, more typically 8-fold or more, and most typically 16-fold or more than for a classical TH2-type cell.

"Memory T cells" as defined herein are a subset of long-lived T cells with prior exposure to a given antigen. Memory T cells can be present in an organism for years, allowing a rapid response to subsequent challenges by the same antigen. The phenotype for mouse memory T cells is defined as CD4+$^{high}$CD45RB$^{low}$. The phenotype of human memory T cells is defined as CD45RA$^{neg/low}$CD45R0$^{high}$. IL-23 treatment of these memory T cells results in proliferation and expression of IL-17.

"Conservatively modified variants" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):
(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Autoimmune condition" or "autoimmune disorder" encompasses, e.g., pathological inflammation, an inflammatory disorder, usually against a self-antigen. "Immune condition" refers to infections, persistent infections, and proliferative conditions, such as cancer, tumors, and angiogenesis, including infections, tumors, and cancers that resist irradication by the immune system. "Cancerous condition" includes, e.g., cancer, cancer cells, tumors, angiogenesis, and precancerous conditions such as dysplasia.

"Inflammatory disorder" and "autoimmune inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

An "IL-17-producing cell" means a T cell that is not a classical TH1-type T cell or classical TH2-type T cell. "IL-17-producing cell" also means a T cell that expresses a gene or polypeptide (e.g., mitogen responsive P-protein; chemokine ligand 2; interleukin-17 (IL-17); transcription factor RoR-γT related; suppressor of cytokine signaling 3, etc.), where expression with treatment by an IL-23 agonist is greater than treatment with an IL-12 agonist, where "greater than" is defined as follows. Expression with an IL-23 agonist is ordinarily at least 5-fold greater, typically at least 10-fold greater, more typically at least 15-fold greater, most typically at least 20-fold greater, preferably at least 25-fold greater, and most preferably at least 30-fold greater, than with IL-12 treatment. Expression can be measured, e.g., with treatment of a population of substantially pure IL-17 producing cells.

Moreover, "IL-17-producing cell" includes a progenitor or precursor cell that is committed, in a pathway of cell development or cell differentiation, to differentiating into an IL-17-producing cell, as defined above. A progenitor or precursor cell to the IL-17 producing cell can be found in a draining lymph node (DLN). Additionally, "IL-17-producing cell" encompasses an IL-17-producing cell, as defined above, that has been, e.g., activated, e.g., by a phorbol ester, ionophore, and/or carcinogen, further differentiated, stored, frozen, desiccated, inactivated, partially degraded, e.g., by apoptosis, proteolysis, or lipid oxidation, or modified, e.g., by recombinant technology.

"Inhibitors" and "antagonists" or "activators" and "agonists" refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Knockout" (KO) refers to the partial or complete reduction of expression of at least a portion of a polypeptide encoded by a gene, e.g., encoding a subunit of IL-23 or IL-23 receptor, where the gene is endogenous to a single cell, selected cells, or all of the cells of a mammal. KO also encompasses embodiments where biological function is reduced, but where expression is not necessarily reduced, e.g., a polypeptide that contains an inserted inactivating peptide. Disruptions in a coding sequence or a regulatory sequence are encompassed by the knockout technique. The cell or mammal may be a "heterozygous knockout", where one allele of the endogenous gene has been disrupted. Alternatively, the cell or mammal may be a "homozygous knockout" where both alleles of the endogenous gene have been disrupted. "Homozygous knockout" is not intended to limit the disruption of both alleles to identical techniques or to identical outcomes at the genome.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, fluorescent dyes, electron-dense reagents, substrates, epitope tags, or enzymes, e.g., as used in enzyme-linked immunoassays, or fluorettes (see, e.g., Rozinov and Nolan (1998) *Chem. Biol.* 5:713-728).

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

A "marker" relates to the phenotype of a cell, tissue, organ, animal, e.g., of an IL-17 producing cell. Markers are used to detect cells, e.g., during cell purification, quantitation, migration, activation, maturation, or development, and may be used for both in vitro and in vivo studies. An activation marker is a marker that is associated with cell activation.

"Purified cell" encompasses, e.g., one or more "IL-17 producing cells" that is substantially free of other types of cells, e.g., contamination by other types of T cells. Purity can be assessed by use of a volume that is defined by geometric coordinates or by a compartment comprising, e.g., a flask, tube, or vial. A "purified IL-17 producing cell" can be defined by, e.g., a compartment where the "IL-17 producing cells" normally constitute at least 20% of all the cells, more normally at least 30% of all the cells, most normally at least 40% of all the cells, generally at least 50% of all the cells, more generally at least 60% of all the cells, most generally at least 70% of all the cells, preferably at least 80% of all the cells, more preferably at least 90% of all the cells; and most preferably at least 95% of all the cells.

"Small molecules" are provided for the treatment of physiology and disorders of the hair follicle. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307: 198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antibody, or binding composition derived thereof. In a preferred embodiment the antibody will have an affinity that is greater than about $10^9$ liters/mol, as determined, e.g., by Scatchard analysis (Munsen, et al. (1980) *Analyt. Biochem.* 107:220-239).

II. General.

The present invention provides methods of using polypeptides, nucleic acids, variants, muteins, and mimetics of IL-23p19 subunit, IL-23 receptor (IL-23R) complex, IL-23R subunit.

Administration of an IL-23, i.e., IL-23 or IL-23 hyperkine, can induce, e.g., proliferation of memory T cells, PHA blasts, CD45RO T cells, CD45RO T cells; enhance production of interferon-gamma (IFNγ) by PHA blasts or CD45RO T cells. In contrast to IL-12, IL-23 preferentially stimulates memory as opposed to naive T cell populations in both human and mouse. IL-23 activates a number of intracellular cell-signaling molecules, e.g., Jak2, Tyk2, Statl, Stat2, Stat3, and Stat4. IL-12 activates this same group of molecules, but Stat4 response to IL-23 is relatively weak, while Stat4 response to IL-12 is strong (Oppmann, et al., supra; Parham, et al. (2002) *J. Immunol.* 168:5699-5708).

Expression of the p19 subunit of IL-23 in mice can result in, e.g., stunted growth, infertility, and death of animals, as well as inflammatory infiltrates, e.g., in the gastrointestinal tract, lungs, skin, and liver, and epithelial cell hyperplasia, microcytic anemia, increased neutrophil count, increased serum tumor necrosis factor-alpha (TNFα); and increased expression of acute phase genes in liver (Wiekowski, et al., supra).

NOD mice were treated with either mouse anti-mIL-23p 19 mAb, rat-anti-mL-17, or with rat anti-mIL-12p40. The group of mice receiving the p19 mAb showed delayed onset (at 22 weeks) and a lower incidence (50% of animals) of diabetes than compared to the anti-p40 treated mice (12 weeks, 84% of animals; see Table 1). Mice treated with anti-IL-17 mAb also showed a lower incidence (50% of animals) of diabetes compared to rat IgG isotype control treated mice (100% of animals). Histological evaluation of insulitits (infiltration of lymphocytes of the islet cells in the pancreas) was performed and graded on a scale of 0 to 4, 0 being normal and 4 being severe infiltrate. At 15 weeks, anti-p19 treated mice showed less infiltrate, whereas diabetic control isotype and anti-p40 treated mice exhibited high levels of grades 3 and 4 insulitits.

TABLE 1

Anti-IL-23p19 and anti-IL-17 but not anti-IL-12p40 inhibited autoimmune diabetes (n = 12-15 mice per group).

| Treatment mAb | Disease onset (age in week) | Disease incidence at 7 month of age |
|---|---|---|
| Anti-IL-23p19 | 22 | 50% |
| mIgG1 | 12 | 77% |
| Anti-IL-12p40 | 12 | 84% |
| rIgG2a | 15 | 84% |
| Anti-IL-17 | 12 | 50% |
| rIgG1 | 12 | 100% |

Anti-p19 treatment resulted in the enhanced mRNA expression of CD4, CD8, and CTLA-4 (CD 152) in the pancreas, suggesting that there are more CTLA-4 positive T cells in the pancreas of anti-IL-23 treated mice as compared to control and anti-p40 treated mice. CTLA-4 is a known marker of regulatory T cells (Tregs), which can control inflammatory or autoimmune responses. A similar result was seen with the expression of GITR, another phenotypic marker of Tregs, and with the expression of MDC (CCL22), a chemokine produced by dendritic cells that may recruit Tregs to inflammatory sites.

III. Antagonists and Binding Compositions.

Antagonists of IL-23 include, e.g., antibodies to IL-23, blocking antibodies to IL-23 receptor, a soluble receptor based on the extracellular region of a subunit of the IL-23 receptor, peptide mimetics thereto, and nucleic acids encoding these antagonists. Binding compositions that specifically bind to p19 of IL-23 or to IL-23R of IL-23 receptor are provided.

Regions of increased antigenicity can be used for antibody generation. Regions of increased antigenicity of human p19 occur, e.g., at amino acids 16-28; 57-87; 110-114; 136-154; and 182-186 of GenBankAAQ89442 (gi:37183284). Regions of increased antigenicity of human IL-23R occur, e.g., at amino acids 22-33; 57-63; 68-74; 101-112; 117-133; 164-177; 244-264; 294-302; 315-326; 347-354; 444-473; 510-530; and 554-558 of GenBank AAM44229 (gi: 21239252). Analysis was by a Parker plot using Vector NTI® Suite (Informax, Inc, Bethesda, Md.). The present invention also provides an IL-23 antagonist that is a soluble receptor, i.e., comprising an extracellular region of IL-23R, e.g., amino acids 1-353 of GenBankAAM44229, or a fragment thereof, where the extracellular region or fragment thereof specifically binds to IL-23. Mouse IL-23R is GenBank NP_653131 (gi: 21362353). Muteins and variants are contemplated, e.g., pegylation or mutagenesis to remove or replace deamidating Asn residues.

An antagonist of an IL-17 producing cell encompasses a reagent that specifically modulates the activity of an IL-17 producing cell, e.g., without substantial influence on the activity of, e.g., a naïve T cell, TH1-type T cell, TH2-type T cell, epithelial cell, and/or endothelial cell. The reagent can modulate expression or activity of, e.g., a transcription factor or adhesion protein, of the IL-17 producing cell.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; U.S. Pat. No. 6,329,511 issued to Vasquez, et al.).

Purification of antigen is not necessary for the generation of antibodies. Immunization can be performed by DNA vector immunization, see, e.g., Wang, et al. (1997) *Virology* 228: 278-284. Alternatively, animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7:283-290; Wright, et al. (2000) *Immunity* 13:233-242; Preston, et al. (1997) *Eur. J Immunol.* 27:1911-1918). Resultant hybridomas can be screened for production of the desired antibody by functional assays or biological assays, that is, assays not dependent on possession of the purified antigen. Immunization with cells may prove superior for antibody generation than immunization with purified antigen (Kaithamana, et al. (1999) *J. Immunol.* 163:5157-5164).

Antibody to antigen and ligand to receptor binding properties can be measured, e.g., by surface plasmon resonance (Karlsson, et al. (1991) *J. Immunol. Methods* 145:229-240; Neri, et al. (1997) *Nat. Biotechnol.* 15:1271-1275; Jonsson, et al. (1991) *Biotechniques* 11:620-627) or by competition ELISA (Friguet, et al. (1985) *J. Immunol. Methods* 77:305-319; Hubble (1997) *Immunol. Today* 18:305-306). Antibodies can be used for affinity purification to isolate the antibody's target antigen and associated bound proteins, see, e.g., Wilchek, et al. (1984) *Meth. Enzymol.* 104:3-55.

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res. (Suppl.)* 9:3982s-3990s).

Soluble receptors comprising the extracellular domains of IL-23R or IL-12Rbeta1 receptor polypeptides are provided. Soluble receptors can be prepared and used according to standard methods (see, e.g., Jones, et al. (2002) *Biochim. Biophys. Acta* 1592:251-263; Prudhomme, et al. (2001) *Expert Opinion Biol. Ther.* 1:359-373; Fernandez-Botran (1999) *Crit. Rev. Clin. Lab Sci.* 36:165-224).

IV. Therapeutic Compositions, Methods.

The invention provides anti-IL-23 and anti-IL-23R for use, e.g., in the treatment of inflammatory and autoimmune disorders. Nucleic acids are also provided for these therapeutic uses, e.g., nucleic acids encoding IL-23 or IL-23R, or an antigenic fragment thereof, the corresponding anti-sense nucleic acids, and hybridization products thereof. The invention also provides compositions for RNA interference (see, e.g., Arenz and Schepers (2003) *Naturwissenschaften* 90:345-359; Sazani and Kole (2003) *J. Clin. Invest.* 112:481-486; Pirollo, et al. (2003) *Pharmacol. Therapeutics* 99:55-77; Wang, et al. (2003) *Antisense Nucl. Acid Drug Devel.* 13:169-189.

To prepare pharmaceutical or sterile compositions including an agonist or antagonist of IL-23, the cytokine analogue or mutein, antibody thereto, or nucleic acid thereof, is admixed with a pharmaceutically acceptable carrier or excipient, see, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

The route of administration is by, e.g., topical or cutaneous application, injection or infusion by intravenous, intraperitoneal, intracerebral, intramuscular, intraocular, intraarterial, intracerebrospinal, intralesional, or pulmonary routes, or by sustained release systems or an implant. Injection of gene transfer vectors into the central nervous system has been described (see, e.g., Cua, et al. (2001) *J. Immunol.* 166:602-608; Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-.1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

An effective amount for a particular patient may vary depending on factors such as the condition being treated, the overall health of the patient, the method route and dose of administration and the severity of side affects, see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art, see, e.g., Hardman, et al. (eds.) (2001) *Goodman and Gilman's The Pharmacological Basis of Therapeutics*, $10^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa. An effective amount of therapeutic will decrease the symptoms typically by at least 10%; usually by at least 20%; preferably at least about 30%; more preferably at least 40%, and most preferably by at least 50%.

V. Kits and Diagnostic Reagents.

This invention provides IL-23 proteins, fragments thereof, nucleic acids, and fragments thereof, in a diagnostic kit. Also provided are binding compositions, including antibodies or antibody fragments, for the detection of IL-23 and IL-23 receptor, and metabolites and breakdown products thereof. Typically, the kit will have a compartment containing either a p19 polypeptide, or an antigenic fragment thereof, a binding composition thereto, or a nucleic acid, e.g., a nucleic acid probe or primer.

The kit may comprise, e.g., a reagent and a compartment, a reagent and instructions for use, or a reagent with a compartment and instructions for use. The reagent may comprise an IL-23 or IL-23R, or an antigenic fragment thereof, a binding composition, or a nucleic acid. A kit for determining the binding of a test compound, e.g., acquired from a biological sample or from a chemical library, can comprise a control compound, a labeled compound, and a method for separating free labeled compound from bound labeled compound.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals (see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162:2804-2811; Everts, et al. (2002) *New Engl. J. Med.* 168:883-889). Various assay formats exist, such as radioimmunoassays (RIA), ELISA, and lab on a chip (U.S. Pat. Nos. 6,176,962 and 6,517,234).

This invention provides polypeptides and nucleic acids of IL-23 and IL-23R, fragments thereof, in a diagnostic kit, e.g., for the diagnosis of inflammatory disorders metabolic system.

Also provided are binding compositions, including antibodies or antibody fragments, for the detection of IL-23 and IL-23R and metabolites and breakdown products thereof. Typically, the kit will have a compartment containing either a IL-23 or IL-23R polypeptide, or an antigenic fragment thereof, a binding composition thereto, or a nucleic acid, such as a nucleic acid probe, primer, or molecular beacon (see, e.g., Rajendran, et al. (2003) *Nucleic Acids Res.* 31:5700-5713; Cockerill (2003) *Arch. Pathol. Lab. Med.* 127:1112-1120; Zammatteo, et al. (2002) *Biotech. Annu. Rev.* 8:85-101; Klein (2002) *Trends Mol. Med.* 8:257-260).

A method of diagnosis can comprise contacting a sample from a subject, e.g., a test subject, with a binding composition that specifically binds to a polypeptide or nucleic acid of IL-23 or IL-23R. The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

The kit may comprise, e.g., a reagent and a compartment, a reagent and instructions for use, or a reagent with a compartment and instructions for use. The reagent may comprise an agonist or antagonist of IL-23 or IL-23R, or an antigenic fragment thereof, a binding composition, or a nucleic acid in a sense and/or anti-sense orientation. A kit for determining the binding of a test compound, e.g., acquired from a biological sample or from a chemical library, can comprise a control compound, a labeled compound, and a method for separating free labeled compound from bound labeled compound.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals (see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162:2804-2811; Everts, et al. (2002) *New Engl. J. Med.* 168:883-889). Various assay formats exist, such as radioimmunoassays (RIA), ELISA, and lab on a chip (U.S. Pat. Nos. 6,176,962 and 6,517,234).

VI. Uses

Due to the prolonged asymptomatic preclinical period in the development of diabetes, IL-23 and IL-23R antagonist therapy can be commenced upon analysis of various genetic and clinical markers of diabetes. Patients exhibiting altered, e.g., lowered, serum levels of insulin II as compared to normal non-diabetic patients can be given IL-23 or IL-23R antagonist therapy to prevent the autoimmune reaction in pancreas and stop the onset of clinical manifestation of diabetes. Patients with high serum levels of C-reactive protein, a known marker for diabetes, may also benefit from IL-23 and IL-23R antagonist therapy to prevent the development of diabetes. Similar treatment may be used for patients having high serum titers of Islet Cell Antibodies (ICAs), patients diagnosed with impaired glucose homeostasis, e.g., between 110 and 126 mg per dL of plasma glucose in a fasting glucose test or between 140 and 200 mg per dL in a glucose load test, or for those patients showing a gradual drop in insulin production (see, e.g., Ziegler, supra.).

Antagonists of IL-23 and IL-23R may be used alone or in conjunction with other inflammatory cytokine antagonists or agonists (e.g., IL-12 antagonists; TNFα antagonists; IL-6 antagonists; IL-17 antagonists; or IL-10 agonists.). IL-23 and IL-23R may also be co-administered with known immunosuppressants, such as azathionine, prednisone, and cyclosporin.

Also envisioned is the use of IL-23 and IL-23R antagonists in conjunction with the engrafting of ex vivo cultured islet cells or progenitors thereof, to prevent reoccurring islet cell destruction. IL-23 and IL-23R antagonists may also be administered to patients receiving pancreatic organ transplants to inhibit predisposed inflammation as well as tissue rejection. The antagonists of IL-23 and IL-23R can also be administered to patients diagnosed with mild diabetes to prevent further destruction of islet cells and exacerbation of the clinical disease.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLES

I. General Methods.

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp.384-391). Production, purification, and fragmentation of polyclonal and monoclonal antibodies is described (Coligan, et al. (2001) *Current Protcols in Immunology*, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology*, Vol. 4, John Wiley, Inc., New York).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCyphe® (TimeLogic Corp., Crystal Bay, Nev.); Menne, et al. (2000) *Bioinformatics* 16:741-742; Menne, et al. (2000) *Bioinformatics Applications Note* 16:741-742; Wren, et al. (2002) *Comput. Methods Programs Biomed.* 68:177-181; von Heijne (1983) *Eur. J Biochem.* 133:17-21; von Heijne (1986) *Nucleic Acids Res.* 14:4683-4690).

II. Quantitative PCR Analysis of NOD Mice Tissues

Total cellular mRNA from pancreatic tissues of NOD mice treated with control mAb, anti-IL-23p19 mAb, or anti-p40 mAb was isolated and reverse transcribed. 50 ng of DNA from each treatment group was analyzed for expression of CD4, CD8, CTLA-4 (CD152), MDC (CCL22), and GITR. Quantitative PCR was performed using the flourogenic 5'-nuclease PCR assay using the ABI Prism 7700 Sequence Detection system (PerkinElmer, Foster City, Calif.) as described in Oppmann, et al. supra. All samples were normalized to a housekeeping gene, e.g., ubiquitin III. Disease Progression in NOD Mice NOD mice were selected at 10 weeks of age for treatment with anti-p 19 mAb. Criteria for selection included little to no evidence of glucose in the urine (glycosuria). Selected animals were treated for 4 weeks, three times a week, with 5mg/kg mouse anti-p19 mAb, rat anti-IL-17mAb, or rat anti-p40 mAb. Antibodies were administered subcutaneously. Efficacy of both treatment groups was compared to isotype control antibodies. Five animals from each treatment group were sacrificed at 15 weeks of age. The remaining animals were followed for several months.

IV. Histological Evaluation of Insulitis

Mice were sacrificed by CO2 asphyxiation, and pancreases were removed, fixed in 10% formalin, and embedded in paraffin blocks. Sections were stained with hematoxylin and eosin for light microscopy. Histopathology was performed to correlate pathological lesions of insulitis with clinical signs of diabetes (glucosuria) in drug treated and non-treated NOD mice. The intensity of insulitis was graded as distribution of lymphoid infiltrates: 0=Normal; 1=perivascular and/or periductal inflammation; 2=Peri-insulitis; 3=Mild insulitis (<25% of islet infiltrated); 4=Severe insulitis (≧25% of islet infiltrated).

What is claimed is:

1. A method of treating an individual predisposed to develop insulin-dependent diabetes mellitus (IDDM) comprising administering an effective amount of:

a) an anti-IL-23p19 antagonist antibody, or an antigen binding fragment thereof, or an anti-IL-23R antagonist antibody, or an antigen binding fragment thereof; and
b) an anti-IL-17 antagonist antibody, or an antigen binding fragment thereof.

2. The method of claim 1, wherein at least one of the anti-IL-23p19 or anti-IL-23R antibodies, or antigen binding fragments thereof, or the anti-IL-17 antibody, or antigen binding fragment thereof, is a monoclonal antibody, or antigen binding fragment thereof.

3. The method of claim 1, further comprising administering an immunosuppressive agent.

4. The method of claim 3, wherein the immunosuppressive agent is:
a) prednisone;
b) azathioprine; or
c) cyclosporin.

5. The method of claim 1, wherein the individual exhibits signs of impaired glucose homeostasis.

6. The method of claim 5, wherein impaired glucose homeostasis is measured by plasma glucose levels either during fasting or after a glucose load.

7. The method of claim 6, wherein the plasma glucose levels are:
a) between 110 to 126 mg per dL during fasting; or
b) between 140 and 200 mg per dL after a glucose load.

8. The method of claim 5, wherein at least one of the anti-IL-23p19 or anti-IL-23R antibodies, or antigen binding fragments thereof, or the anti-IL-17 antibody, or antigen binding fragment thereof, is a monoclonal antibody, or antigen binding fragment thereof.

9. The method of claim 8, further comprising administering an immunosuppressive agent.

10. The method of claim 9, wherein the immunosuppressive agent is:
a) prednisone;
b) azathioprine; or
c) cyclosporin.

11. The method of claim 1, wherein at least one of the anti-IL-23p19 or anti-IL-23R antibodies, or antigen binding fragments thereof, or the anti-IL-17 antibody, or antigen binding fragment thereof, is a humanized antibody, or antigen binding fragment thereof.

12. The method of claim 1, wherein at least one of the anti-IL-23p19 or anti-IL-23R antibodies, or antigen binding fragments thereof, or the anti-IL-17 antibody, or antigen binding fragment thereof, is an Fab, Fv, or F(ab')$_2$ fragment.

13. The method of claim 1, wherein at least one of the anti-IL-23p19 or anti-IL-23R antibodies, or antigen binding fragments thereof, or the anti-IL-17 antibody, or antigen binding fragment thereof, is a single chain antibody.

14. The method of claim 1, wherein an anti-IL-23p19 antagonist antibody, or antigen binding fragment thereof, is administered in step (a).

15. The method of claim 1, wherein an anti-IL-23R antagonist antibody, or antigen binding fragment thereof, is administered in step (a).

16. The method of claim 5, wherein at least one of the anti-IL-23p19 or anti-IL-23R antibodies, or antigen binding fragments thereof, or the anti-IL-17 antibody, or antigen binding fragment thereof, is a humanized antibody, or antigen binding fragment thereof.

17. The method of claim 5, wherein at least one of the anti-IL-23p19 or anti-IL-23R antibodies, or antigen binding fragments thereof, or the anti-IL-17 antibody, or antigen binding fragment thereof, is an Fab, Fv, or F(ab')$_2$ fragment.

18. The method of claim 5, wherein at least one of the anti-IL-23p19 or anti-IL-23R antibodies, or antigen binding fragments thereof, or the anti-IL-17 antibody, or antigen binding fragment thereof, is a single chain antibody.

19. The method of claim 1, wherein the individual exhibits signs of impaired glucose homeostasis, and an anti-IL-23p19 antagonist antibody, or antigen binding fragment thereof, is administered in step (a).

20. The method of claim 1, wherein the individual exhibits signs of impaired glucose homeostasis, and an anti-IL-23R antagonist antibody, or antigen binding fragment thereof, is administered in step (a).

* * * * *